US007846101B2

(12) United States Patent
Eberle et al.

(10) Patent No.: US 7,846,101 B2
(45) Date of Patent: *Dec. 7, 2010

(54) HIGH RESOLUTION INTRAVASCULAR ULTRASOUND TRANSDUCER ASSEMBLY HAVING A FLEXIBLE SUBSTRATE

(75) Inventors: Michael J. Eberle, Fair Oaks, CA (US); Douglas N. Stephens, Davis, CA (US); Gary Rizzuti, Shingle Springs, CA (US); Horst Kiepen, Georgetown, CA (US); Andreas Hodjicostis, Everett, WA (US)

(73) Assignee: Volcano Corporation, Rancho Cordova, CA (US)

( * ) Notice: Subject to any disclaimer, the term of this patent is extended or adjusted under 35 U.S.C. 154(b) by 402 days.

This patent is subject to a terminal disclaimer.

(21) Appl. No.: 11/757,816

(22) Filed: Jun. 4, 2007

(65) Prior Publication Data

US 2007/0239024 A1 Oct. 11, 2007

Related U.S. Application Data

(63) Continuation of application No. 08/712,576, filed on Sep. 13, 1996, now Pat. No. 7,226,417, which is a continuation of application No. 08/578,226, filed on Dec. 26, 1995, now abandoned.

(51) Int. Cl.

| | |
|---|---|
| *A61B 8/14* | (2006.01) |
| *H01L 41/22* | (2006.01) |
| *H04R 17/00* | (2006.01) |
| *H04R 31/00* | (2006.01) |
| *H05K 3/00* | (2006.01) |

(52) U.S. Cl. ...................... 600/459; 600/467; 29/25.35; 29/594; 29/829

(58) Field of Classification Search .................. 600/459
See application file for complete search history.

(56) References Cited

U.S. PATENT DOCUMENTS 4,231,154 A 11/1980 Gazdik et al.

(Continued)

FOREIGN PATENT DOCUMENTS

EP 0 145 429 A2 6/1985

(Continued)

OTHER PUBLICATIONS

Black et al., "CMOS Chips for Invasive Ultrasound Imaging," *IEEE Journal of Solid-State Circuits*, 29 (11) 1381-1387 (1994).

(Continued)

*Primary Examiner*—Long V Le
*Assistant Examiner*—Hien Nguyen
(74) *Attorney, Agent, or Firm*—Haynes and Boone LLP

(57) ABSTRACT

An ultrasound transducer assembly of the present invention includes a flexible circuit to which an ultrasound transducer array and integrated circuitry are attached during fabrication of the ultrasound transducer assembly. The flexible circuit comprises a flexible substrate to which the integrated circuitry and transducer elements are attached while the flexible substrate is in a substantially flat shape. The flexible circuit further comprises electrically conductive lines that are deposited upon the flexible substrate. The electrically conductive lines transport electrical signals between the integrated circuitry and the transducer elements. After assembly, the flexible circuit is re-shapable into a final form such as, for example, a substantially cylindrical shape.

20 Claims, 10 Drawing Sheets

U.S. PATENT DOCUMENTS

| | | | |
|---|---|---|---|
| 4,440,025 A | 4/1984 | Hayakawa et al. | |
| 4,564,980 A | 1/1986 | Diepers | |
| 4,641,660 A | 2/1987 | Bele | |
| 4,645,961 A | 2/1987 | Malsky | |
| 4,665,331 A | 5/1987 | Sudo et al. | |
| 4,704,774 A | 11/1987 | Fujii et al. | |
| 4,728,834 A | 3/1988 | Kumar et al. | |
| 4,734,963 A | 4/1988 | Ishiyama | |
| 4,841,977 A | 6/1989 | Griffith et al. | |
| 4,869,768 A | 9/1989 | Zola | |
| 4,917,097 A | 4/1990 | Proudian et al. | |
| 4,962,329 A | 10/1990 | Fujita et al. | |
| 4,975,607 A | 12/1990 | Hara et al. | |
| 5,042,493 A | 8/1991 | Saito et al. | |
| 5,044,053 A | 9/1991 | Kopel et al. | |
| 5,081,993 A | 1/1992 | Kitney et al. | |
| 5,109,860 A | 5/1992 | Gelly et al. | |
| 5,135,001 A | 8/1992 | Sinofsky et al. | |
| 5,167,233 A | 12/1992 | Eberle et al. | |
| 5,176,141 A | 1/1993 | Bom et al. | |
| 5,186,177 A | 2/1993 | O'Donnell et al. | |
| 5,240,003 A | 8/1993 | Lancee et al. | |
| 5,240,004 A | 8/1993 | Walinsky et al. | |
| 5,243,988 A | 9/1993 | Sieben et al. | |
| 5,257,629 A | 11/1993 | Kitney et al. | |
| 5,275,167 A | 1/1994 | Killam | |
| 5,320,104 A | 6/1994 | Fearnside et al. | |
| 5,351,691 A | 10/1994 | Brommersma | |
| 5,359,760 A | 11/1994 | Busse et al. | |
| 5,368,037 A | 11/1994 | Eberle et al. | |
| 5,398,689 A | 3/1995 | Connor et al. | |
| 5,402,791 A | 4/1995 | Saitoh et al. | |
| 5,453,575 A | 9/1995 | O'Donnell et al. | |
| 5,456,259 A | 10/1995 | Barlow et al. | |
| 5,467,779 A | 11/1995 | Smith et al. | |
| 5,479,930 A | 1/1996 | Gruner et al. | |
| 5,488,957 A | 2/1996 | Frey et al. | |
| 5,740,808 A | 4/1998 | Panescu et al. | |
| 5,744,898 A * | 4/1998 | Smith et al. | 310/334 |
| 5,793,541 A | 8/1998 | Cattan et al. | |
| 6,110,314 A | 8/2000 | Nix et al. | |
| 6,238,347 B1 | 5/2001 | Nix et al. | |
| 6,776,763 B2 | 8/2004 | Nix et al. | |
| 7,226,417 B1 * | 6/2007 | Eberle et al. | 600/467 |

FOREIGN PATENT DOCUMENTS

| | | | |
|---|---|---|---|
| EP | 0 671 221 | B1 | 4/2000 |
| GB | 2 258 364 | A | 2/1993 |
| GB | 2 287 375 | A | 9/1995 |
| JP | 54149165 | A2 | 11/1979 |
| WO | WO 88/09150 | A1 | 12/1988 |
| WO | WO 94/17734 | A1 | 8/1994 |

OTHER PUBLICATIONS

O'Donnell et al., "Experimental Studies on an Efficient Catheter Array Imaging System" *Ultrasonic Imaging*, 17(2). 83-94 (1995).

Bom et al., "Early and Recent Intraluminal Ultrasound Devices," International Journal of Cardiac Imaging, vol. 4, pp. 79-88, 1989.

* cited by examiner

HIGH RESOLUTION INTRAVASCULAR ULTRASOUND TRANSDUCER ASSEMBLY HAVING A FLEXIBLE SUBSTRATE

This application is a continuation of application Ser. No. 08/712,576, filed Sep. 13, 1996, which is a continuation of application Ser. No. 08/578,226, filed Dec. 26, 1995. The contents of U.S. patent application Ser. No. 08/712,576 are incorporated by reference in their entirety, including any references contained therein.

FIELD OF THE INVENTION

This invention relates to ultrasound imaging apparatuses placed within a cavity to provide images thereof of the type described in Proudian et al. U.S. Pat. No. 4,917,097 and more specifically, to ultrasound imaging apparatuses and methods for fabricating such devices on a scale such that the transducer assembly portion of the imaging apparatus may be placed within a vasculature in order to produce images of the vasculature.

BACKGROUND OF THE INVENTION

In the United States and many other countries, heart disease is a leading cause of death and disability. One particular kind of heart disease is atherosclerosis, which involves the degeneration of the walls and lumen of the arteries throughout the body. Scientific studies have demonstrated the thickening of an arterial wall and eventual encroachment of the tissue into the lumen as fatty material builds upon the vessel walls. The fatty material is known as "plaque." As the plaque builds up and the lumen narrows, blood flow is restricted. If the artery narrows too much, or if a blood clot forms at an injured plaque site (lesion), flow is severely reduced, or cut off and consequently the muscle that it supports may be injured or die due to a lack of oxygen. Atherosclerosis can occur throughout the human body, but it is most life threatening when it involves the coronary arteries which supply oxygen to the heart. If blood flow to the heart is significantly reduced or cut off, a myocardial infarction or "heart attack" often occurs. If not treated in sufficient time, a heart attack often leads to death.

The medical profession relies upon a wide variety of tools to treat coronary disease, ranging from drugs to open heart "bypass" surgery. Often, a lesion can be diagnosed and treated with minimal intervention through the use of catheter-based tools that are threaded into the coronary arteries via the femoral artery in the groin. For example, one treatment for lesions is a procedure known as percutaneous transluminal coronary angioplasty (PTCA) whereby a catheter with an expandable balloon at its tip is threaded into the lesion and inflated. The underlying lesion is re-shaped, and hopefully, the lumen diameter is increased to improve blood flow.

In recent years, a new technique has been developed for obtaining information about coronary vessels and to view the effects of therapy on the form and structure of a site within a vessel rather then merely determining that blood is flowing through a vessel. The new technique, known as Intracoronary/Intravascular Ultrasound (ICUS/IVUS), employs very small transducers arranged on the end of a catheter which provide electronic transduced echo signals to an external imaging system in order to produce a two or three-dimensional image of the lumen, the arterial tissue, and tissue surrounding the artery. These images are generated in substantially real time and provide images of superior quality to the known x-ray imaging methods and apparatuses. Imaging techniques have been developed to obtain detailed images of vessels and the blood flowing through them. An example of such a method is the flow imaging method and apparatus described in O'Donnell et al. U.S. Pat. No. 5,453,575, the teachings of which are expressly incorporated in their entirety herein by reference. Other imaging methods and intravascular ultrasound imaging applications would also benefit from enhanced image resolution.

Known intravascular ultrasound transducer assemblies have limited image resolution arising from the density of transducer elements that are arranged in an array upon a transducer assembly. Known intravascular transducer array assemblies include thirty-two (32) transducer elements arranged in a cylindrical array. While such transducer array assemblies provide satisfactory resolution for producing images from within a vasculature, image resolution may be improved by increasing the density of the transducer elements in the transducer array.

However, reducing the size of the transducer array elements increases the diffraction of the ultrasound beam emitted by a transducer element which, in turn, leads to decreased signal strength. For example, if the width of each of the currently utilized ferroelectric copolymer transducer elements is reduced by one-half so that sixty-four (64) transducer elements are arranged in a cylindrical array roughly the same size as the thirty-two (32) transducer array, the strength of the signal produced by the individual transducer elements in the sixty-four (64) element array falls below a level that is typically useful for providing an image of a blood vessel. More efficient transducer materials (having a lower "insertion loss") may be substituted for the ferroelectric copolymer transducer material in order to provide a useful signal in an intravascular ultrasound transducer assembly having sixty-four (64) transducer elements in a cylindrical array. Such materials include lead zirconate titanate (PZT) and PZT composites which are normally used in external ultrasound apparatuses. However, PZT and PZT composites present their own design and manufacturing limitations. These limitations are discussed below.

In known ultrasound transducer assemblies, a thin glue layer bonds the ferroelectric copolymer transducer material to the conductors of a carrier substrate. Due to the relative dielectric constants of ferroelectric copolymer and epoxy, the ferroelectric copolymer transducer material is effectively capacitively coupled to the conductors without substantial signal losses when the glue layer thickness is on the order of 0.5 to 2.0 μm for a ferroelectric copolymer film that is 10-15 μm thick. This is a practically achievable glue layer thickness.

However, PZT and PZT composites have a relatively high dielectric constant. Therefore capacitive coupling between the transducer material and the conductors, without significant signal loss could occur only when extremely thin glue layers are employed (e.g. 0.01 μm for a 10-15 μm thick PZT transducer). This range of thicknesses for a glue layer is not achievable in view of the current state of the art.

Transducer backing materials having relatively low acoustic impedance improve signal quality in transducer assemblies comprising PZT or PZT composites. The advantages of such backing materials are explained in Eberle et al. U.S. Pat. No. 5,368,037 the teachings of which are expressly incorporated in their entirety herein by reference. It is also important to select a matching layer for maximizing the acoustic performance of the PZT transducers by minimizing echoes arising from the ultrasound assembly/blood-tissue interface.

Individual ferroelectric copolymer transducers need not be physically isolated from other transducers. However, PZT transducers must be physically separated from other transducers in order to facilitate formation of the transducers into a cylinder and to provide desirable performance of the transducers, such as minimization of acoustic crosstalk between neighboring elements. If the transducer elements are not physically separated, then the emitted signal tends to conduct to the adjacent transducer elements comprising PZT or PZT composite material.

Furthermore, the PZT and PZT composites are more brittle than the ferroelectric copolymer transducer materials, and the transducer elements cannot be fabricated in a solid flat sheet and then re-shaped into a cylindrical shape of the dimensions suitable for internal ultrasound imaging.

The integrated circuitry of known ultrasound transducer probes are mounted upon a non-planar surface. (See, for example, the Proudian '097 patent). The fabrication of circuitry on a non-planar surface adds complexity to the processes for mounting the integrated circuitry and connecting the circuitry to transmission lines connecting the integrated circuitry to a transmission cable and to the transducer array.

Yet another limitation on designing and manufacturing higher density ultrasound transducer arrays for intravascular imaging is the density of the interconnection circuitry between the ultrasound transducer elements and integrated circuits placed upon the ultrasound transducer assembly. Presently an interconnection density of about 0.002" pitch between connection points is achievable using state-of-the-art fabrication techniques. However, in order to arrange sixty-four (64) elements in a cylindrical array having a same general construction and size (i.e., 1.0 mm) as the previously known 32 element array (e.g., the array disclosed in the Proudian et al. U.S. Pat. No. 4,917,097), the interconnection circuit density would have to increase. The resulting spacing of the interconnection circuitry would have to be reduced to about 0.001" pitch. Such a circuit density is near the limits of current capabilities of the state of the art for reasonable cost of manufacturing.

SUMMARY OF THE INVENTION

It is a general object of the present invention to improve the image quality provided by an ultrasound imaging apparatus over known intravascular ultrasound imaging apparatuses.

It is another object of the present invention to decrease the per-unit cost for manufacturing ultrasound transducer assemblies.

If is yet another object of the present invention to increase the yield of manufactured ultrasound transducer assemblies.

It is a related object to increase image resolution by substantially increasing the number of transducer elements in a transducer array while substantially maintaining the size of the transducer array assembly.

The above mentioned and other objects are met in a new ultrasound transducer assembly and method for fabricating the ultrasound transducer assembly incorporating a flexible substrate. The ultrasound transducer assembly of the present invention includes a flexible circuit comprising a flexible substrate and electrically conductive lines, deposited upon the flexible substrate. An ultrasound transducer array and integrated circuitry are attached during fabrication of the ultrasound transducer assembly while the flexible substrate is substantially planar (i.e., flat). After assembly the electrically conductive lines transport electrical signals between the integrated circuitry and the transducer elements.

The ultrasound transducer array comprises a set of ultrasound transducer elements. In an illustrative embodiment, the transducer elements are arranged in a cylindrical array. However, other transducer array arrangements are contemplated, such as linear, curved linear or phased array devices.

The integrated circuitry is housed within integrated circuit chips on the ultrasound transducer assembly. The integrated circuitry is coupled via a cable to an imaging computer which controls the transmission of ultrasound emission signals transmitted by the integrated circuitry to the ultrasound transducer array elements. The imaging computer also constructs images from electrical signals transmitted from the integrated circuitry corresponding to ultrasound echoes received by the transducer array elements.

The above described new method for fabricating an ultrasound catheter assembly retains a two-dimensional aspect to the early stages of ultrasound transducer assembly fabrication which will ultimately yield a three-dimensional, cylindrical device. Furthermore, the flexible circuit and method for fabricating an ultrasound transducer assembly according to the present invention facilitate the construction of individual, physically separate transducer elements in a transducer array.

BRIEF DESCRIPTION OF THE DRAWINGS

The appended claims set forth the features of the present invention with particularity. The invention, together with its objects and advantages, may be best understood from the following detailed description taken in conjunction with the accompanying drawings of which:

Figures 1, 1A:
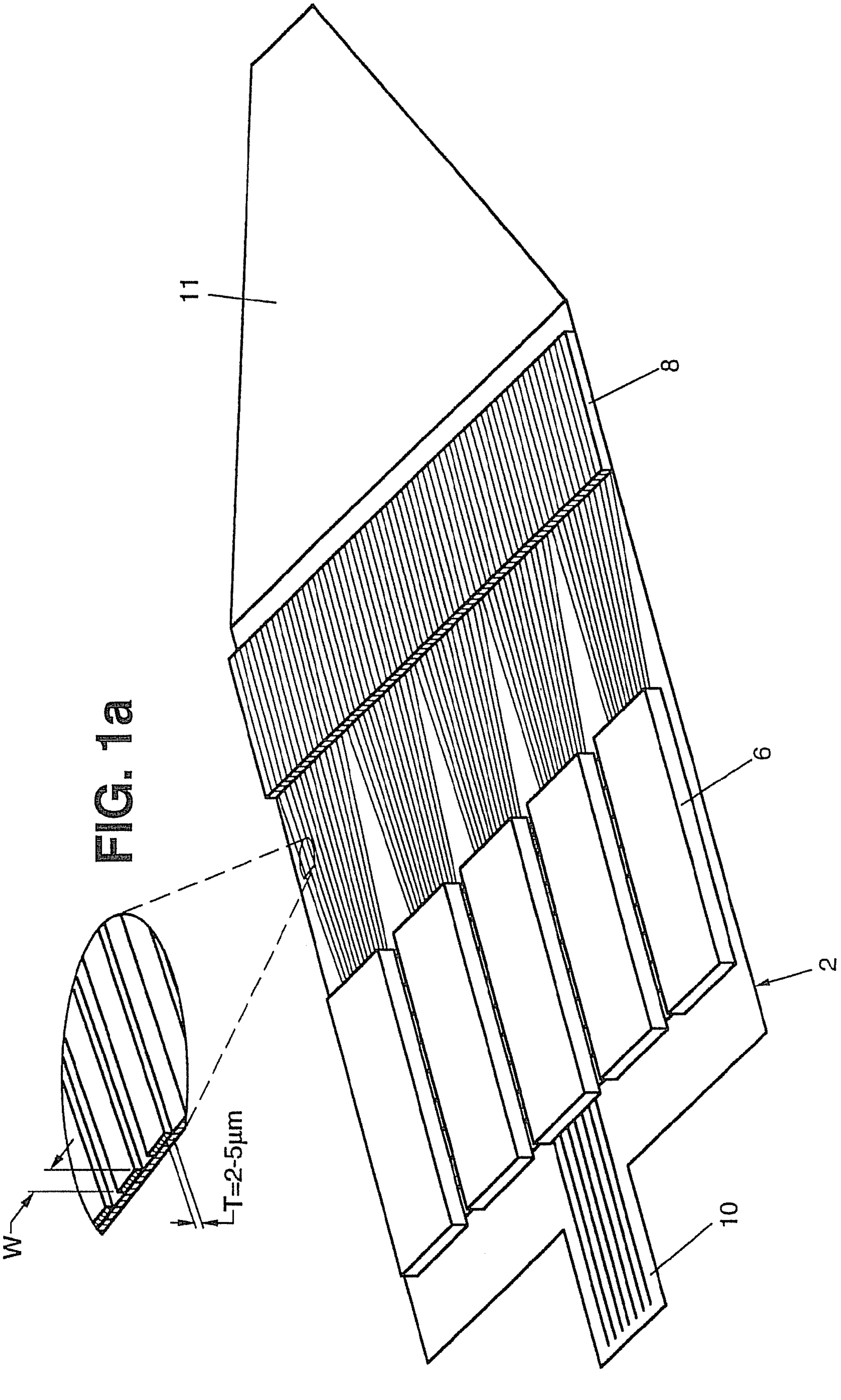
FIG. 1 is a perspective view of the flat sub-assembly of an ultrasound transducer assembly incorporating a 64 element ultrasound transducer array and integrated circuits mounted to a flexible circuit.
Figures 5, 5A:
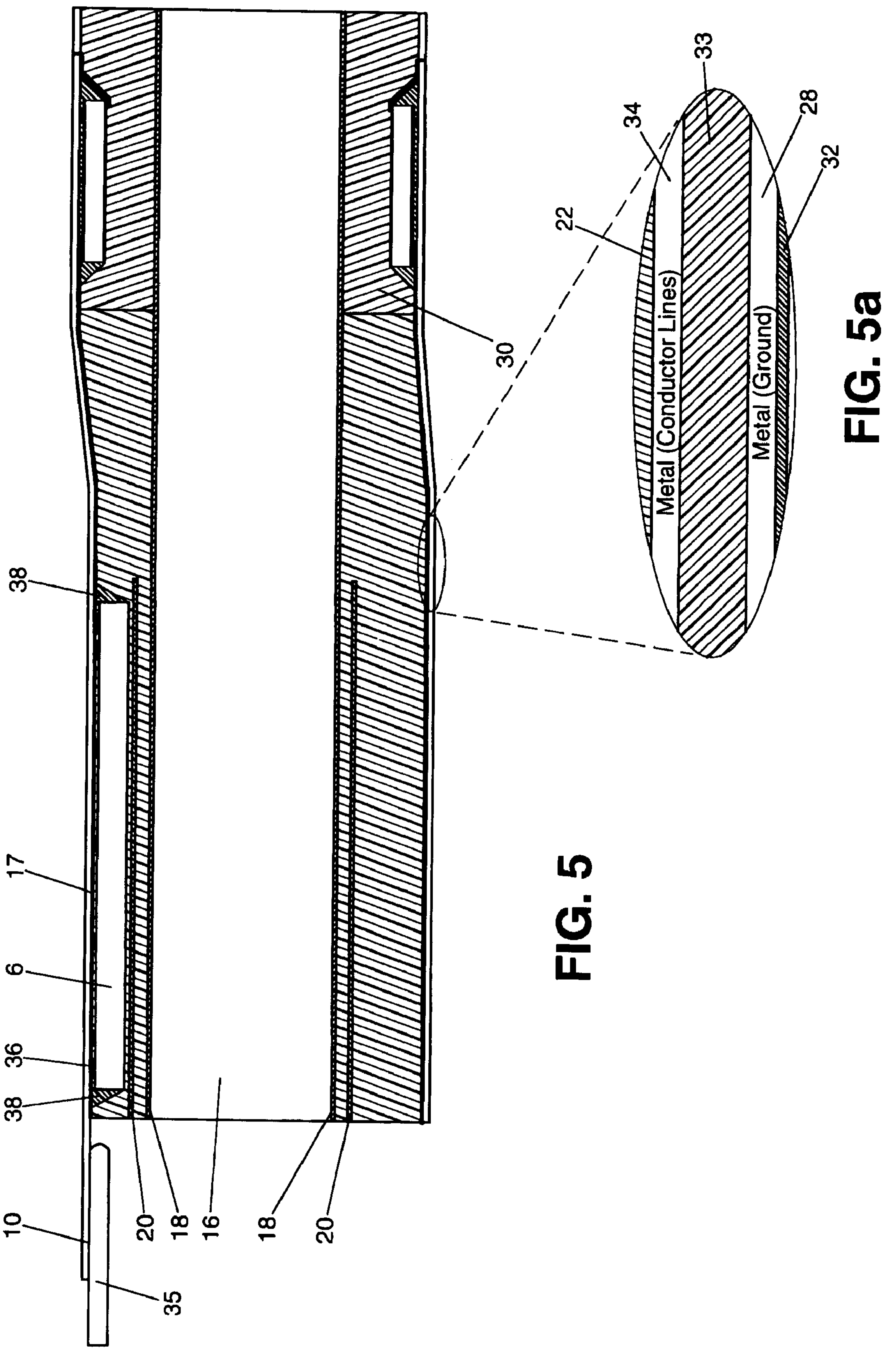
FIG. 5 is a longitudinal cross-section view of the ultrasound transducer assembly illustrated in FIG. 2 sectioned along line 5-5 and running along the length of the ultrasound transducer assembly.
Figure 6:
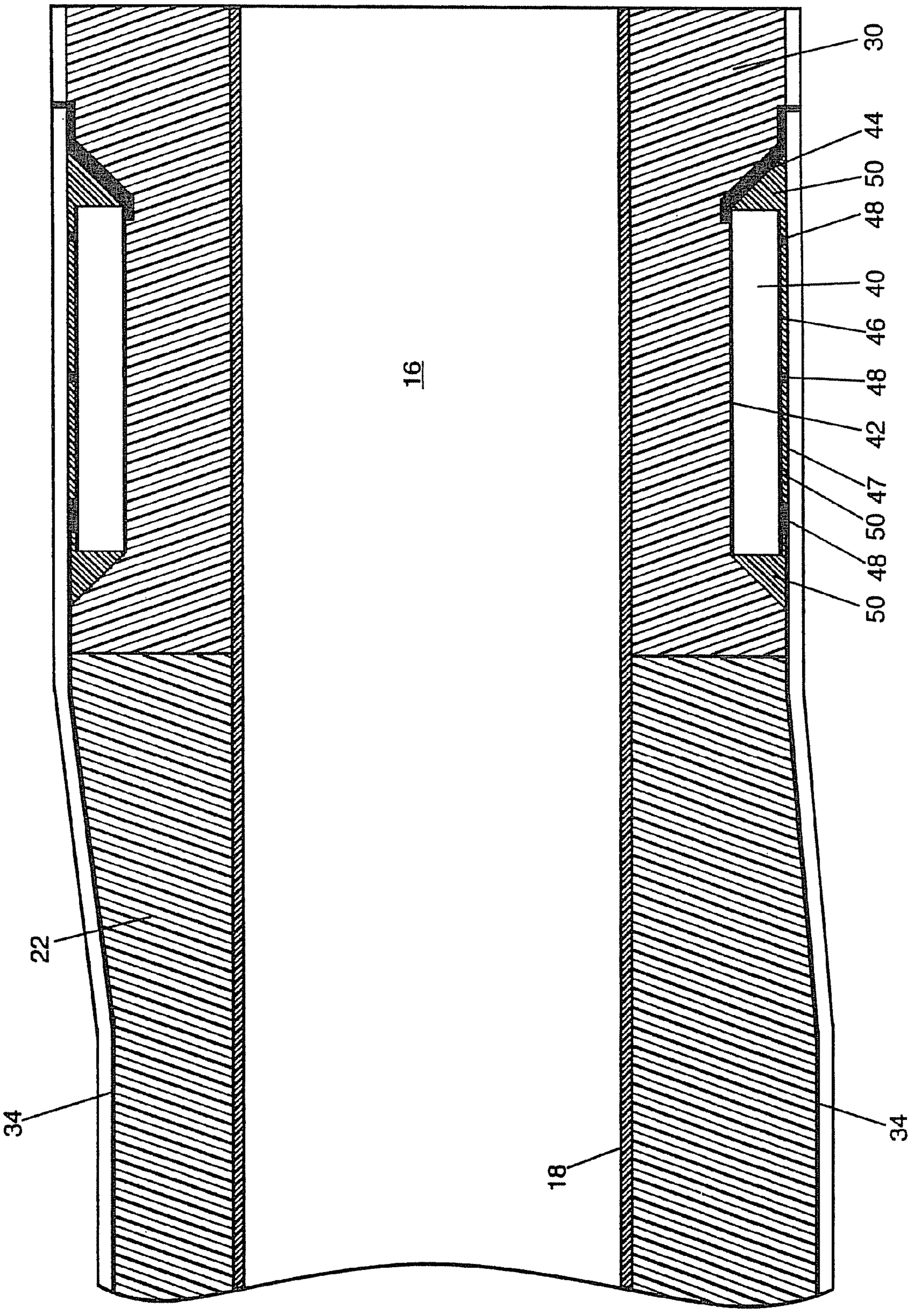
Figure 7:
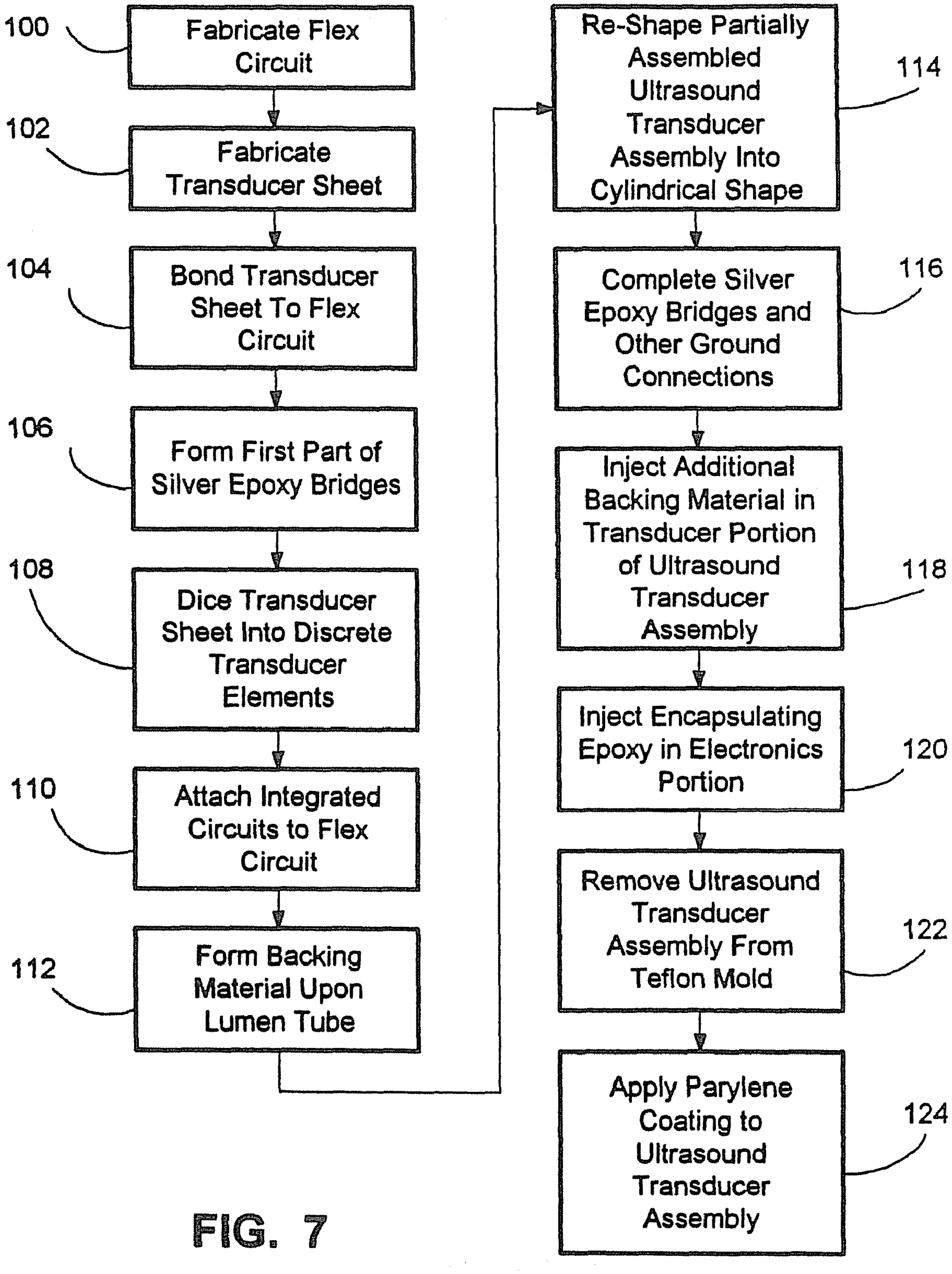
Figure 8:
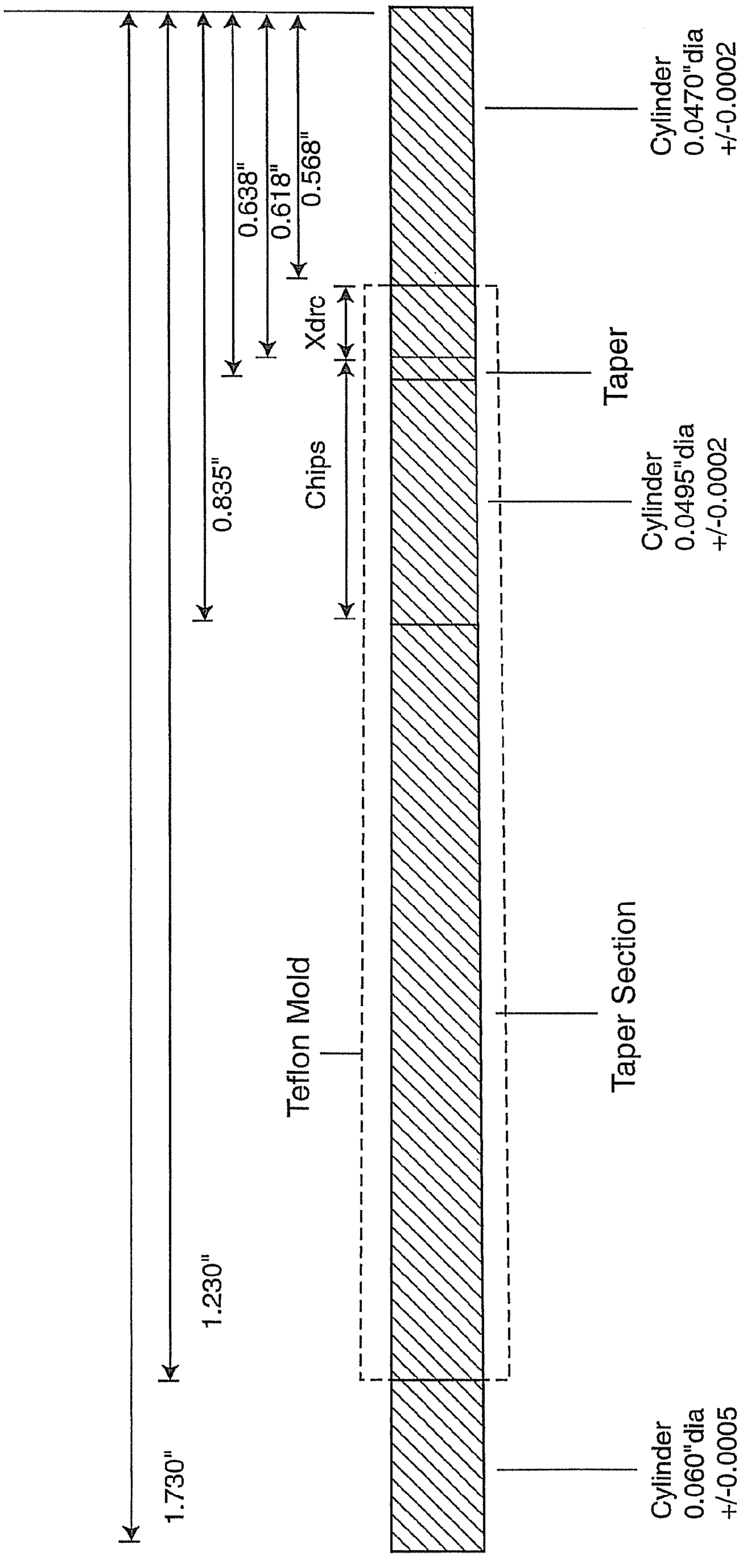
Figure 9:
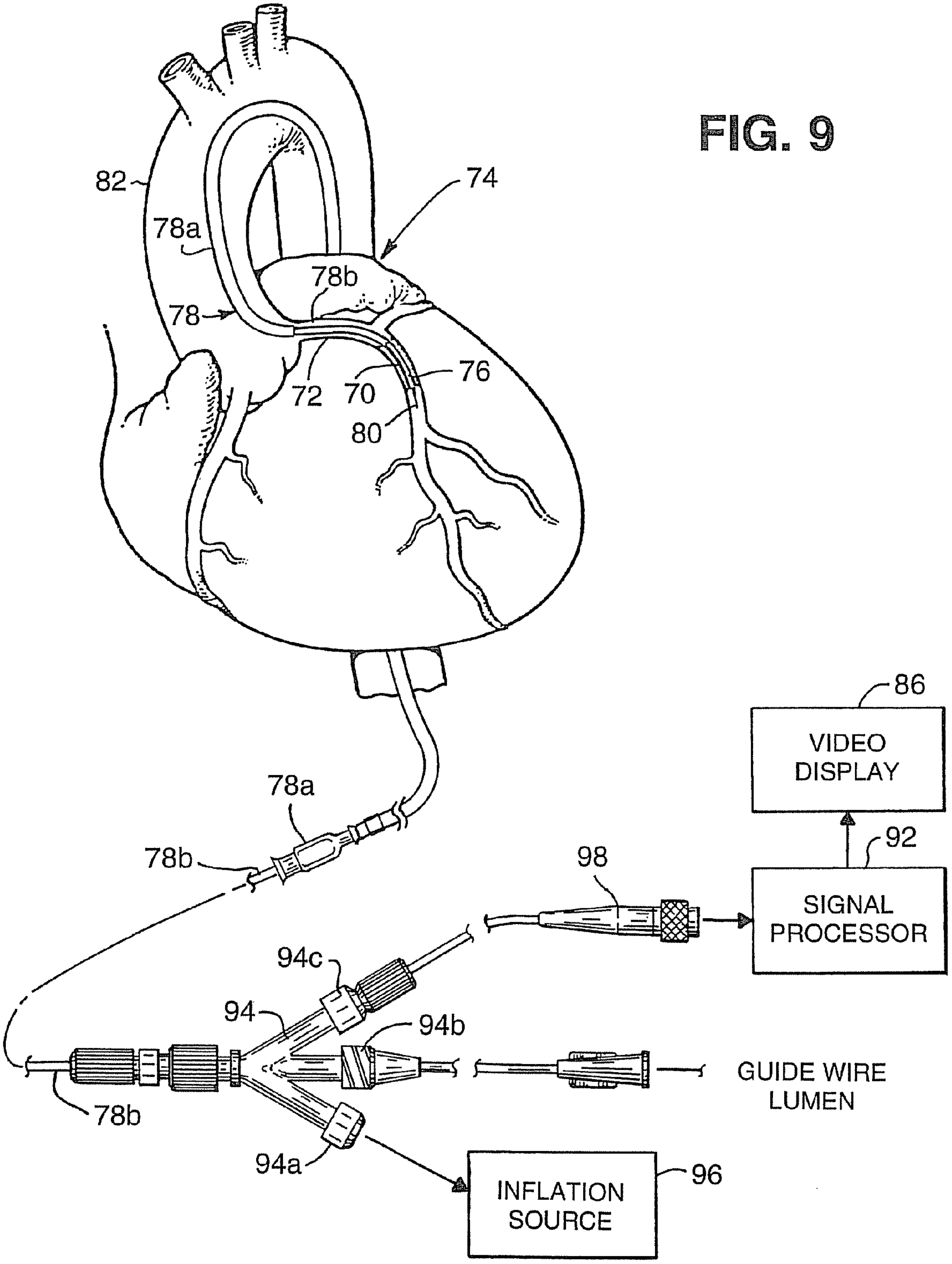
Figure 10:
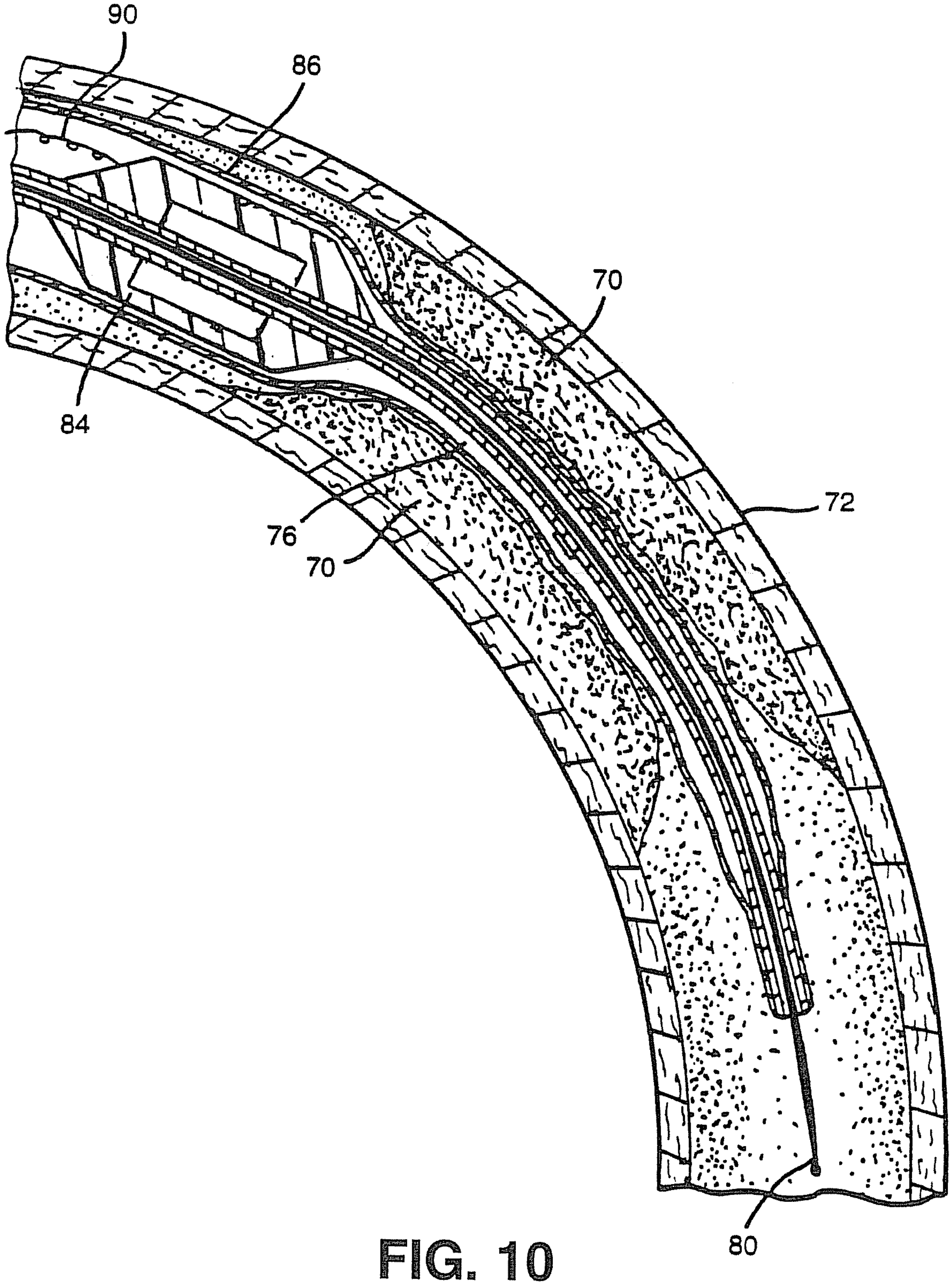

FIG. **5*a* is an enlarged view of the outer layers of the sectioned view of the ultrasound transducer assembly illustratively depicted in FIG. 5**;

FIG. 6 is an enlarged and more detailed view of the transducer region of the ultrasound transducer assembly illustratively depicted in FIG. 5;

FIG. **6*a*** is a further enlarged view of a portion of the transducer region containing a cross-sectioned transducer;

FIG. 7 is a flowchart summarizing the steps for fabricating a cylindrical ultrasound transducer assembly embodying the present invention;

FIG. 8 is a schematic drawing showing a longitudinal cross-section view of a mandrel used to form a mold within which a partially assembled ultrasound transducer assembly is drawn in order to re-shape the flat, partially assembled transducer assembly into a substantially cylindrical shape and to thereafter finish the ultrasound catheter assembly in accordance with steps 114-120 of FIG. 7;

FIG. 9 is a schematic drawing of an illustrative example of an ultrasound imaging system including an ultrasound transducer assembly embodying the present invention and demonstrating the use of the device to image a coronary artery; and FIG. 10 is an enlarged and partially sectioned view of a portion of the coronary artery in FIG. 1 showing the ultrasound transducer assembly incorporated within an ultrasound probe assembly located in a catheter proximal to a balloon and inserted within a coronary artery.

DETAILED DESCRIPTION OF THE DRAWINGS

Turning now to FIG. 1, a new ultrasound transducer assembly is illustratively depicted in its flat form in which it is assembled prior to forming the device into its final, cylindrical form. The ultrasound transducer assembly comprises a flex circuit 2, to which the other illustrated components of the ultrasound transducer assembly are attached. The flex circuit 2 preferably comprises a flexible polyimide film layer (substrate) such as KAPTON™ by DuPont. However, other suitable flexible and relatively strong materials, such as MYLAR (Registered trademark of E.I. DuPont) may comprise the film layer of the flex circuit 2. The flex circuit 2 further comprises metallic interconnection circuitry formed from a malleable metal (such as gold) deposited by means of known sputtering, plating and etching techniques employed in the fabrication of microelectronic circuits upon a chromium adhesion layer on a surface of the flex circuit 2.

The interconnection circuitry comprises conductor lines deposited upon the surface of the flex circuit 2 between a set of five (5) integrated circuit chips 6 and a set of sixty-four (64) transducer elements 8 made from PZT or PZT composites; between adjacent ones of the five (5) integrated circuit chips; and between the five (5) integrated circuit chips and a set of cable pads 10 for communicatively coupling the ultrasound catheter to an image signal processor via a cable (not shown). The cable comprises, for example, seven (7) 43 AWG insulated magnet wires, spirally cabled and jacketed within a thin plastic sleeve. The connection of these seven cables to the integrated circuit chips 6 and their function are explained in Proudian (deceased) et al. U.S. Pat. No. 4,917,097.

The width "W" of the individual conductor lines of the metallic circuitry (on the order of one-thousandth of an inch) is relatively thin in comparison to the typical width of metallic circuitry deposited upon a film or other flexible substrate. On the other hand, the width of the individual conductor lines is relatively large in comparison to the width of transmission lines in a typical integrated circuit. The layer thickness "T" of the conductor lines between the chips 6 and the transducer elements 8 is preferably 2-5 μm. This selected magnitude for the thickness and the width of the conductor lines enables the conductor lines to be sufficiently conductive while maintaining relative flexibility and resiliency so that the conductor lines do not break during re-shaping of the flex circuit 2 into a cylindrical shape.

The thickness of the flex circuit 2 substrate is preferably on the order of 12.5 μm to 25.0 μm. However, the thickness of the substrate is generally related to the degree of curvature in the final assembled transducer assembly. The thin substrate of the flex circuit 2, as well as the relative flexibility of the substrate material, enables the flex circuit 2 to be wrapped into a generally cylindrical shape after the integrated circuit chips 6 and the transducer elements 8 have been mounted and formed and then attached to the metallic conductors of the flex circuit 2. Therefore, in other configurations, designs, and applications requiring less or more substrate flexibility such as, for example, the various embodiments shown in Eberle et al. U.S. Pat. No. 5,368,037, the substrate thickness may be either greater or smaller than the above mentioned range. Thus, a flexible substrate thickness may be on the order of several (e.g. 5) microns to well over 100 microns (or even greater)—depending upon the flexibility requirements of the particular transducer assembly configuration.

The flex circuit is typically formed into a very small cylindrical shape in order to accommodate the space limitations of blood vessels. In such instances the range of diameters for the cylindrically shaped ultrasound transducer assembly is typically within the range of 0.5 mm. to 3.0 mm. However, it is contemplated that the diameter of the cylinder in an ultrasound catheter for blood vessel imaging may be on the order of 0.3 mm. to 5 mm. Furthermore, the flex circuit 2 may also be incorporated into larger cylindrical transducer assemblies or even transducer assemblies having alternative shapes including planar transducer assemblies where the flexibility requirements imposed upon the flex circuit 2 are significantly relaxed. A production source of the flex circuit 2 in accordance with the present invention is Metrigraphics Corporation, 80 Concord Street, Wilmington, Mass. 01887.

The integrated circuit chips 6 are preferably of a type described in the Proudian et al. U.S. Pat. No. 4,917,097 (incorporated herein by reference) and include the modifications to the integrated circuits described in the O'Donnell et al. U.S. Pat. No. 5,453,575 (also incorporated herein by reference). However, both simpler and more complex integrated circuits may be attached to the flex circuit 2 embodying the present invention. Furthermore, the integrated circuit arrangement illustrated in FIG. 1 is intended to be illustrative. Thus, the present invention may be incorporated into a very wide variety of integrated circuit designs and arrangements are contemplated to fall within the scope of the invention.

Finally, the flex circuit 2 illustratively depicted in FIG. 1 includes a tapered lead portion 11. As will be explained further below, this portion of the flex circuit 2 provides a lead into a TEFLON (registered trademark of E.I. DuPont) mold when the flex circuit 2 and attached components are re-shaped into a cylindrical shape. Thereafter, the lead portion 11 is cut from the re-shaped flex circuit 2.

Figure 2:
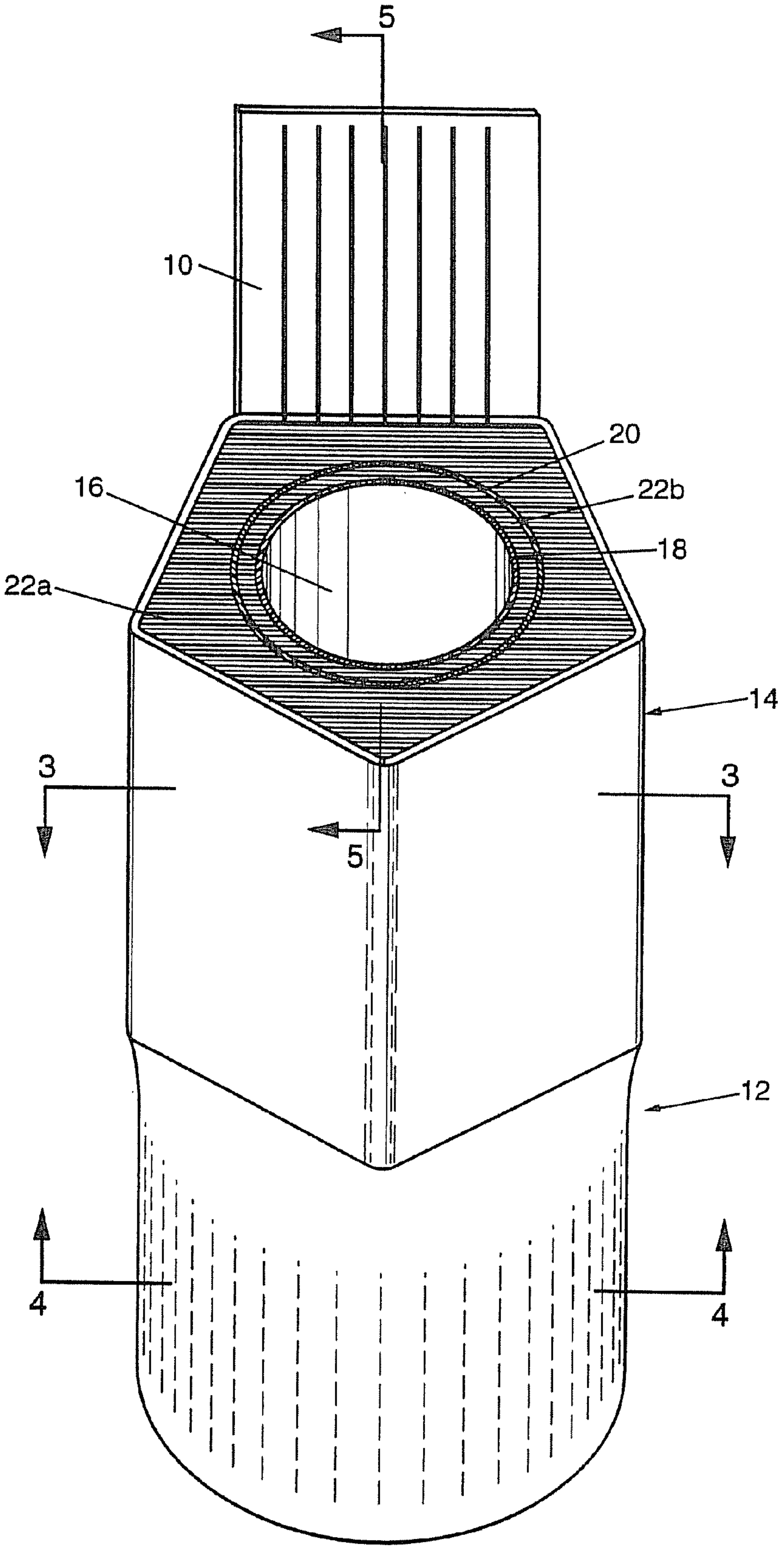
FIG. 2 is a schematic perspective view of the assembled ultrasound transducer assembly from the end containing the cable attachment pad.

Turning to FIG. 2, an ultrasound transducer assembly is shown in a re-shaped state. This shape is generally obtained by wrapping the flat, partially assembled ultrasound transducer assembly shown in FIG. 1 into a cylindrical shape by means of a molding process described below. A transducer portion 12 of the ultrasound transducer assembly containing the transducer elements 8 is shaped in a cylinder for transmitting and receiving ultrasound waves in a generally radial direction in a side-looking cylindrical transducer array arrangement. The transducer portion 12 on which the transducer elements 8 are placed may alternatively be shaped or oriented in a manner different from the cylinder illustratively depicted in FIG. 2 in accordance with alternative fields of view such as side-fire planar arrays and forward looking planar or curved arrays.

The electronics portion 14 of the ultrasound transducer assembly is not constrained to any particular shape. However, in the illustrative example the portions of the flex circuit 2 which support the integrated circuits are relatively flat as a result of the electrical connections between the flex circuit and the integrated circuits. Thus the portion of the flex circuit 2 carrying five (5) integrated circuit chips 6 has a pentagon cross-section when re-shaped (wrapped) into a cylinder. In an alternative embodiment of the present invention, a re-shaped flex circuit having four (4) integrated circuits has a rectangular cross-section. Other numbers of integrated circuits and resulting cross-sectional shapes are also contemplated.

FIG. 2 also shows the set of cable pads 10 on the flex circuit 2 which extend from the portion of the flex circuit 2 supporting the integrated circuit chips 6. A lumen 16 in the center of the ultrasound transducer assembly (within which a guidewire is threaded during the use of a catheter upon which the transducer assembly has been mounted) is defined by a lumen tube 18 made of a thin radiopaque material such as Platinum/Iridium. The radiopaque material assists in locating the ultrasound transducer assembly within the body during a medical procedure incorporating the use of the ultrasound transducer assembly.

Encapsulating epoxy 22*a* and 22*b* fills the spaces, respectively, between the integrated circuit chips 6 and a KAPTON tube 20, and a region between the lumen tube 18 and the KAPTON tube 20 in the re-shaped ultrasound transducer assembly illustrated in FIG. 2. The manner in which the encapsulating epoxy is applied during construction of the ultrasound transducer device embodying the present invention is described below in conjunction with FIG. 7 which summarizes the steps for fabricating such an ultrasound transducer assembly. The KAPTON tube 20 helps to support the integrated circuits 6 during formation of the flex circuit 2 into the substantially cylindrical shaped device illustrated in FIG. 2. A more detailed description of the layers of the transducer portion 12 and the electronics portion 14 of the ultrasound transducer assembly of the present invention is provided below.

Figure 3:
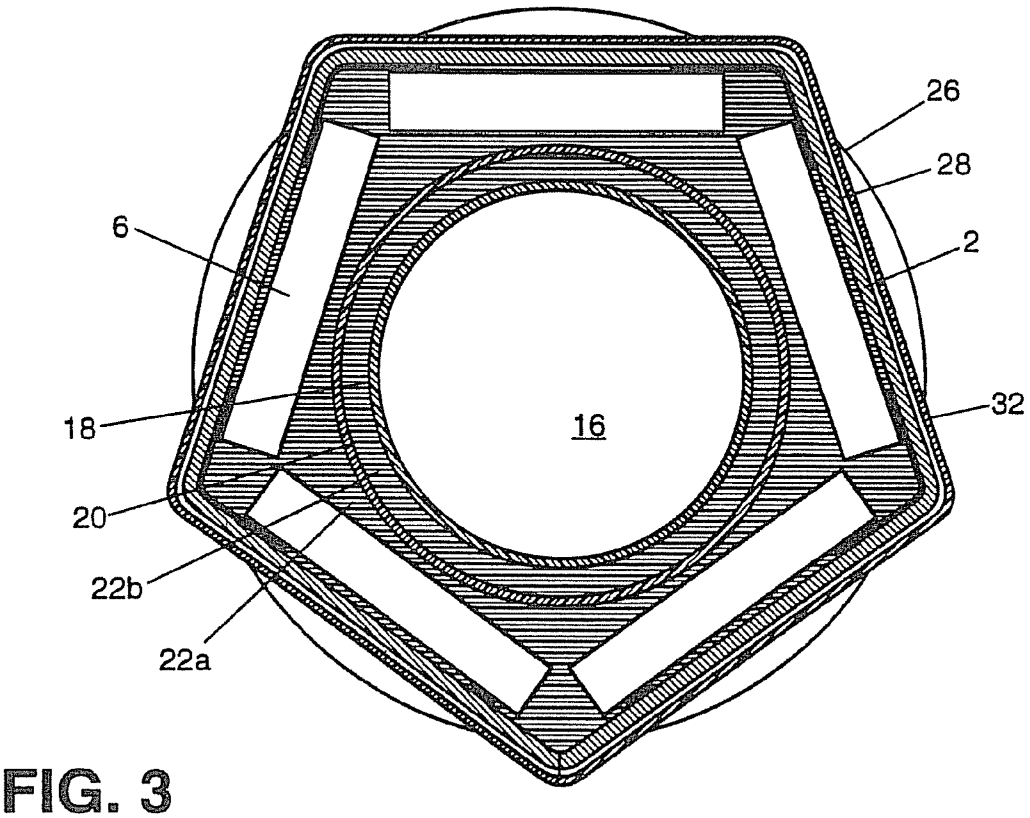
FIG. 3 is a cross-section view of the ultrasound transducer assembly illustrated in FIG. 2 sectioned along line 3-3 in the integrated circuit portion of the ultrasound transducer assembly.

Turning now to FIG. 3, a cross-section view is provided of the ultrasound transducer assembly taken along line 3-3 and looking toward the transducer portion 12 in FIG. 2. The outside of the electronics portion 14 has a pentagon shape. The circular outline 26 represents the outside of the transducer portion 12. The entire ultrasound transducer assembly is electrically shielded by a ground layer 28. The ground layer 28 is encapsulated within a PARYLENE (registered trademark of Union Carbide) coating 32.

Figure 4:
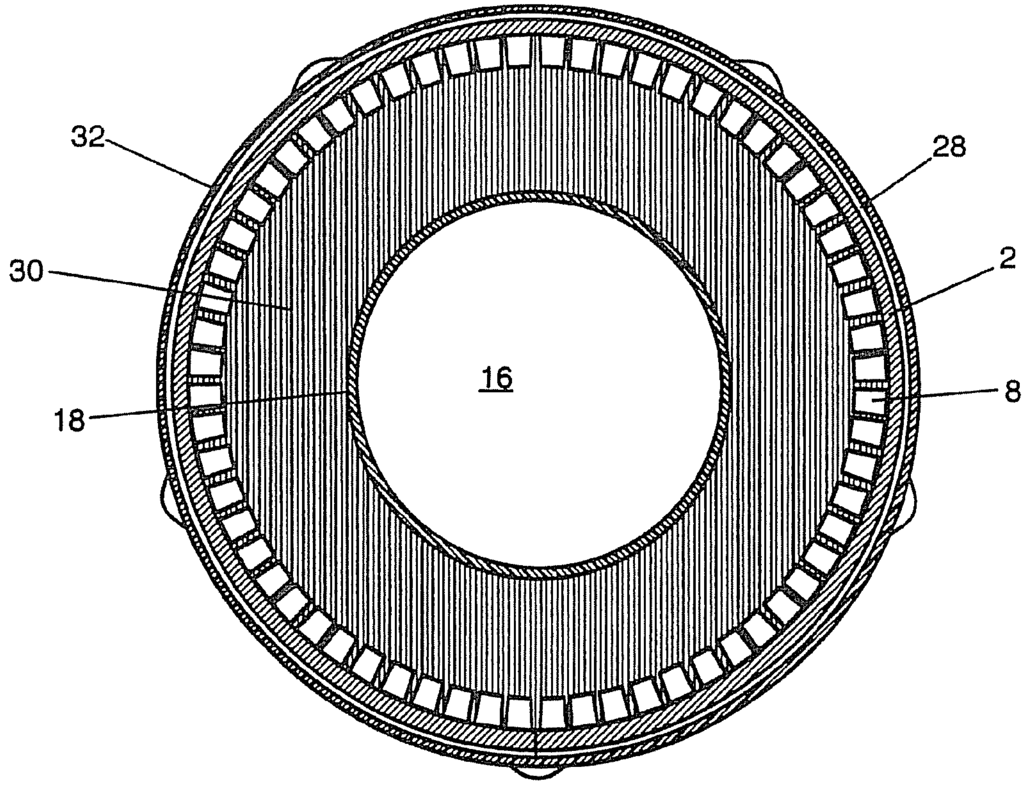
FIG. 4 is a cross-section view of the ultrasound transducer assembly illustrated in FIG. 2 sectioned along line 4-4 in the transducer portion of the ultrasound transducer assembly.

Turning now to FIG. 4, a view is provided of a cross-section of the ultrasound transducer assembly taken along line 4-4 and looking toward the electronics portion 14 in FIG. 2. The five corners of the pentagon outline comprising the electronics portion 14 are illustrated in the background of the cross-sectional view at line 4-4. The set of sixty-four (64) transducer elements 8 are displayed in the foreground of this cross-sectional view of the transducer portion 12 of the ultrasound transducer assembly. A backing material 30 having a relatively low acoustic impedance fills the space between the lumen tube 18 and the transducer elements 8 as well as the gaps between adjacent ones of the sixty-four (64) transducer elements 8. The backing material 30 possesses the ability to highly attenuate the ultrasound which is transmitted by the transducer elements 8. The backing material 30 also provides sufficient support for the transducer elements. The backing material 30 must also cure in a sufficiently short period of time to meet manufacturing needs. A number of known materials meeting the above described criteria for a good backing material will be known to those skilled in the art. An example of such a preferred backing material comprises a mixture of epoxy, hardener and phenolic microballoons providing high ultrasound signal attenuation and satisfactory support for the ultrasound transducer assembly.

Having generally described an ultrasound transducer assembly incorporating the flex circuit in accordance with the present invention, the advantages provided by the flex circuit will now be described in conjunction with the illustrative embodiment. The flex circuit 2 provides a number of advantages over prior ultrasound transducer assembly designs. The ground layer 28, deposited on the flex circuit 2 while the flex circuit is in the flat state, provides an electrical shield for the relatively sensitive integrated circuit chips 6 and transducer elements 8. The KAPTON substrate of the flex circuit 2 provides acoustic matching for the PZT transducer elements 8, and the PARYLENE outer coating 32 of the ultrasound transducer assembly provides a second layer of acoustic matching as well as a final seal around the device.

The ease with which the flex circuit 2 may be re-shaped facilitates mounting, formation and connection of the integrated circuit chips 6 and transducer elements 8 while the flex circuit 2 is flat, and then re-shaping the flex circuit 2 into its final state after the components have been mounted, formed and connected. The flex circuit 2 is held within a frame for improved handling and positioning while the PZT and integrated circuits are bonded to complete the circuits. The single sheet of PZT or PZT composite transducer material is diced into sixty-four (64) discrete transducer elements by sawing or other known cutting methods. After dicing the transducer sheet, kerfs exist between adjacent transducer elements while the flex circuit 2 is in the flat state. After the integrated circuit chips 6 and transducer elements 8 have been mounted, formed and connected, the flex circuit 2 is re-shaped into its final, cylindrical shape by drawing the flex circuit 2 and the mounted elements into a TEFLON mold (described further below).

Also, because the integrated circuits and transducer elements of the ultrasound transducer assembly may be assembled while the flex circuit 2 is in the flat state, the flex circuit 2 may be manufactured by batch processing techniques wherein transducer assemblies are assembled side-by-side in a multiple-stage assembly process. The flat, partially assembled transducer assemblies are then re-shaped and fabrication completed.

Furthermore, it is also possible to incorporate strain relief in the catheter assembly at the set of cable pads 10. The strain relief involves flexing of the catheter at the cable pads 10. Such flexing improves the durability and the positionability of the assembled ultrasound catheter within a patient.

Another important advantage provided by the flex circuit 2, is the relatively greater amount of surface area provided in which to lay out connection circuitry between the integrated circuit chips 6 and the transducer elements 8. In the illustrated embodiment of the present invention, the transducer array includes sixty-four (64) individual transducer elements. This is twice the number of transducer elements of the transducer array described in the Proudian '097 patent. Doubling the number of transducer elements without increasing the circumference of the cylindrical transducer array doubles the density of the transducer elements. If the same circuit layout described in the Proudian '097 was employed for connecting the electronic components in the sixty-four (64) transducer element design, then the density of the connection circuitry between the integrated circuit chips 6 and the transducer elements 8 must be doubled.

However, the flex circuit 2 occupies a relatively outer circumference of: (1) the transducer portion 12 in comparison to the transducer elements 8 and, (2) the electronics portion 14 in comparison to the integrated circuit chips 6. The relatively outer circumference provides substantially more area in which to lay out the connection circuitry for the sixty-four (64) transducer element design in comparison to the area in which to lay out the connection circuitry in the design illustratively depicted in the Proudian '097 patent. As a result, even though the number of conductor lines between the integrated circuit chips 6 and the transducer elements 8 doubles, the density of the conductor lines is increased by only about fifty percent (50%) in comparison to the previous carrier design disclosed in the Proudian ’097 patent having a substantially same transducer assembly diameter.

Yet another advantage provided by the flex circuit 2 of the present invention is that the interconnection solder bumps, connecting the metallic pads of the integrated circuit chips 6 to matching pads on the flex circuit 2, are distributed over more of the chip 3 surface, so the solder bumps only have to be slightly smaller than the previous design having only 32 transducer elements.

The integrated circuit chips 6 are preferably bonded to the flex circuit 2 using known infrared alignment and heating methods. However, since the flex circuit 2 can be translucent, it is also possible to perform alignment with less expensive optical methods which include viewing the alignment of the integrated circuit chips 6 with the connection circuitry deposited upon the substrate of the flex circuit 2 from the side of the flex circuit 2 opposite the surface to which the integrated circuit chips 6 are to be bonded.

Turning now to FIGS. 5 and 5*a*, a cross-sectional view and enlarged partial cross-sectional view are provided of the ultrasound transducer assembly illustrated in FIG. 2 sectioned along line 5-5 and running along the length of the ultrasound transducer assembly embodying the present invention. The PARYLENE coating 32, approximately 5-20 μm in thickness, completely encapsulates the ultrasound transducer assembly. The PARYLENE coating 32 acts as an acoustic matching layer and protects the electronic components of the ultrasound transducer assembly.

The next layer, adjacent to the PARYLENE coating 32 is the ground layer 28 which is on the order of 1-2 μm in thickness and provides electrical protection for the sensitive circuits of the ultrasound transducer assembly. The next layer is a KAPTON substrate 33 of the flex circuit 2 approximately 13 μm thick. Metallic conductor lines 34, approximately 2-5 μm in thickness, are bonded to the KAPTON substrate 33 with a chromium adhesion layer to form the flex circuit 2. While the metallic conductor lines 34 of the flex circuit 2 are illustrated as a solid layer in FIG. 5, it will be appreciated by those skilled in the art that the metallic conductor lines 34 are fabricated from a solid layer (or layers) of deposited metal using well known metal layer selective etching techniques such as masking or selective plating techniques. In order to minimize the acoustic affects of the conductive layers, the metal is on the order of 0.1 μm thick in the region of the transducer. A cable 35 of the type disclosed in the Proudian ’097 patent is connected to the cable pads 10 for carrying control and data signals transmitted between the ultrasound transducer assembly and a processing unit.

Next, a set of solder bumps such as solder bump 36 connect the contacts of the integrated circuit chips 6 to the metallic conductor lines 34 of the flex circuit 2. A two-part epoxy 38 bonds the integrated circuit chips 6 to the flex circuit 2. The integrated circuit chips 6 abut the KAPTON tube 20 having a diameter of approximately 0.030" and approximately 25 μm in thickness. The integrated circuit chips 6 are held in place by the KAPTON tube 20 when the opposite side edges of the flex circuit 2 for the partially fabricated ultrasound transducer assembly are joined to form a cylinder.

FIG. 5 also shows the encapsulating epoxy 22 which fills the gaps between the integrated circuits and the space between the KAPTON tube 20 and the lumen tube 18. The lumen tube 18 has a diameter of approximately 0.024" and is approximately 25 μm thick. A region at the transducer portion 12 of the ultrasound transducer assembly is filled by the backing material 30 having a low acoustic impedance in order to inhibit ringing in the ultrasound transducer assembly by absorbing ultrasound waves emitted by the transducer elements toward the lumen tube 18. The transducer portion 12 of the ultrasound transducer assembly of the present invention is described in greater detail below in conjunction with FIGS. 6 and 6*a*.

Figure 6A:
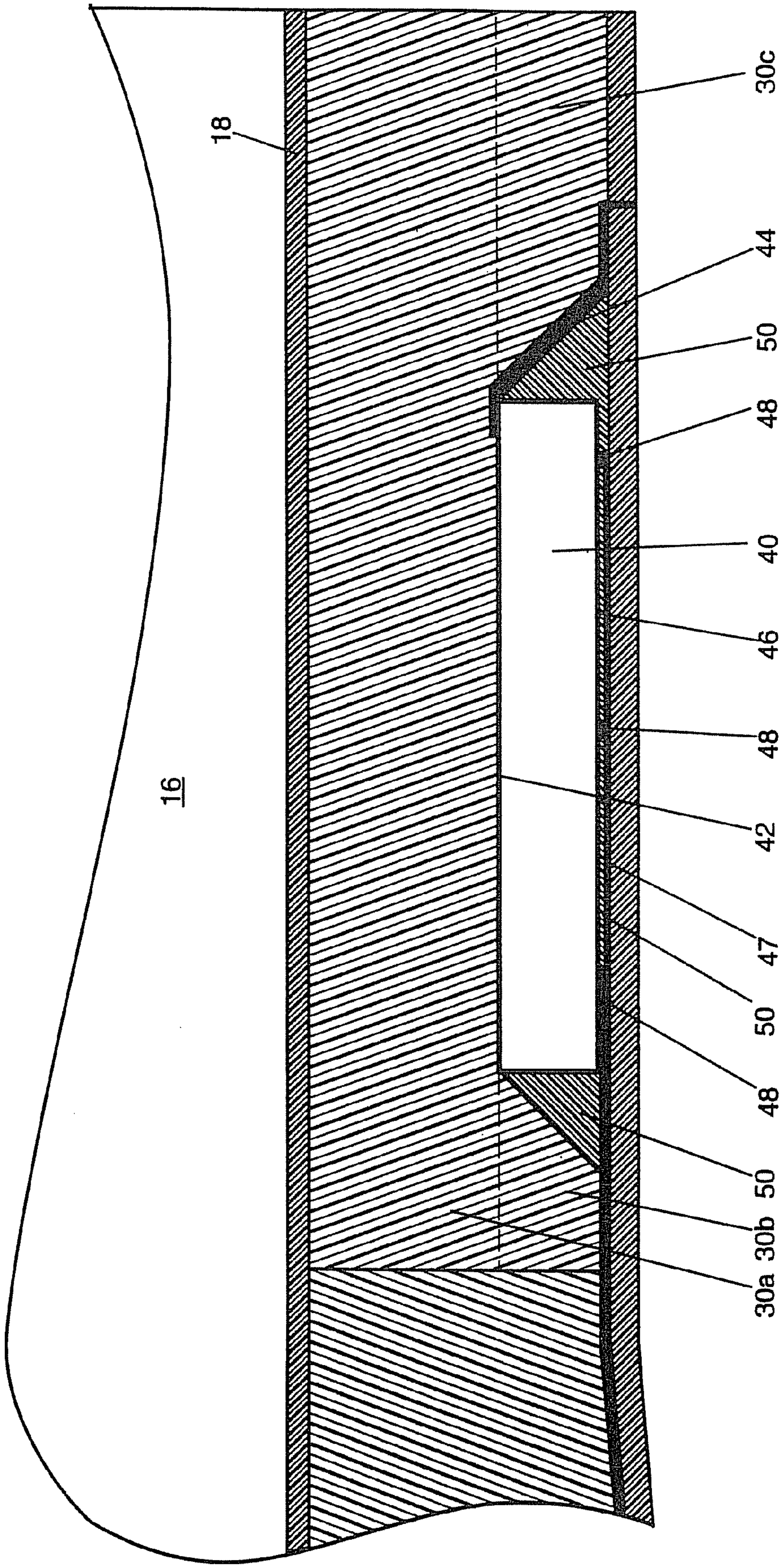

Turning now to FIGS. 6 and 6*a* (an enlarged portion of FIG. 6 providing additional details regarding the structure of the transducer portion 12 of the transducer assembly), the transducer elements 8 comprise a PZT or PZT composite 40 approximately 90 cm in thickness and, depending on frequency, approximately 40 cm wide and 700 μm long. Each transducer element includes a Cr/Au ground layer 42, approximately 0.1 μm in thickness, connected via a silver epoxy bridge 44 to the ground layer 28. Each transducer element includes a Cr/Au electrode layer 46, approximately 0.1 μm in thickness. The Cr/Au electrode layer 46 is directly bonded to the PZT or PZT composite 40. The electrode layer 46 of each transducer element is electrically connected to a corresponding electrode 47 by means of several contacts such as contacts 48. The several contacts for a single transducer are used for purposes of redundancy and reliability and to act as a spacer of constant thickness between the electrode 47 and the PZT composite 40 of a transducer element. Each electrode such as electrode 47 is connected to one of the metallic conductor lines 34 of the flex circuit 2. The thickness of the electrode 47 is less than the thickness of the metallic conductor lines 34 in order to enhance acoustic response of the transducer elements 8. The corresponding conductor line couples the transducer element to an I/O channel of one of the integrated circuit chips 6. A two-part epoxy 50, approximately 2-5 μm in thickness, fills the gaps between the electrode layer 46 and the flex circuit 2 (comprising the substrate 33 and metal layers 34 and 28, and can also be selected to act as an acoustic matching layer.

Finally, as will be explained further below in conjunction with steps 112 and 118 in FIG. 7, the backing material 30 is applied in two separate steps. At step 112, a cylinder 30*a* of backing material is molded directly upon the lumen tube 18. During step 118, the remaining portions 30*b* and 30*c* are injected to complete the backing material portion. It is further noted that while the barrier between the encapsulating epoxy 22 and the backing material 30 is shown as a flat plane in the figures, this barrier is not so precise—especially with respect to the portions 30*b* and 30*c* which are applied by injecting the backing material through the kerfs between adjacent transducers.

Turning now to FIG. 7, the steps are summarized for fabricating the above-described ultrasound transducer assembly embodying the present invention. It will be appreciated by those skilled in the art that the steps may be modified in alternative embodiments of the invention.

At step 100, the flex circuit 2 is formed by depositing layers of conductive materials such as Chromium/Gold (Cr/Au) on a surface of the KAPTON substrate 33. Chromium is first deposited as a thin adhesion layer, typically 50-100 Angstroms thick, followed by the gold conducting layer, typically 2-5 μm thick. Using well known etching techniques, portions of the Cr/Au layer are removed from the surface of the KAPTON substrate 33 in order to form the metallic conductor lines 34 of the flex circuit 2. The ground layer 28, also made up of Cr/Au is deposited on the other surface of the flex circuit 2. The ground layer 28 is typically kept thin in order to minimize its effects on the acoustic performance of the transducer.

During the formation of the conductor lines, the gold bumps, used to make contact between the PZT transducer conductive surface and the conductor lines on the flex circuit, are formed on the flex circuit 2. Also, in the transducer region, as previously stated, the Cr/Au layer is typically kept thin in order to allow a stand-off for the adhesion layer, and so that the metal has a minimum effect on the acoustic performance of the transducer. This can be achieved by performing a secondary metallization stage after the formation of the conducting lines and the gold bumps.

In a separate and independent procedure with respect to the above-described step for fabricating the flex circuit 2, at step 102 metal layers 42 and 46 are deposited on the PZT or PZT composite 40 to form a transducer sheet. Next, at step 104, the metallized PZT or PZT composite 40 is bonded under pressure to the flex circuit 2 using a two-part epoxy 50, and cured overnight. The pressure exerted during bonding reduces the thickness of the two-part epoxy 50 to a thickness of approximately 2-5 μm, depending on the chosen thickness of the gold bumps. The very thin layer of two-part epoxy 50 provides good adhesion of the metallized PZT or PZT composite to the flex circuit 2 without significantly affecting the acoustic performance of the transducer elements 8. During exertion of pressure during step 104, a portion of the two-part epoxy 50 squeezes out from between the flex circuit 2 and the transducer sheet from which the transducer elements 8 will be formed. That portion of the two-part epoxy 50 forms a fillet at each end of the bonded transducer sheet (See FIG. 6). The fillets of the two-part epoxy 50 provide additional support for the transducer elements 8 during sawing of the PZT or PZT composite into separate transducer elements. Additional two-part epoxy 50 may be added around the PZT to make the fillet more uniform.

At step 106, after the two-part epoxy 50 is cured and before the PZT or PZT composite 40 is separated into 64 discrete transducer elements, the first part of the silver epoxy bridges, such as silver epoxy bridge 44, is formed. The silver epoxy bridges conductively connect the ground layer (such as ground layer 42) of the transducer elements 8 to the ground layer 28 on the opposite surface of the flex circuit 2. The silver epoxy bridges such as silver epoxy bridge 44 are formed in two separate steps. During step 106, the majority of each of the silver epoxy bridges is formed by depositing silver epoxy upon the ground layer of the transducer elements 8 such as ground layer 42, the fillet formed on the side of the transducer material by the two-part epoxy 50, and the KAPTON substrate 33. The silver epoxy bridges are completed during a later stage of the fabrication process by filling vias formed in the KAPTON substrate 33 of the flex circuit 2 with silver epoxy material. These vias may be formed by well known "through-hole" plating techniques during the formation of the flex circuit 2, but can also be formed by simply cutting a flap in the relatively thin flex circuit 2 material and bending the flap inward towards the center of the cylinder when the fabricated flex circuit and components are re-shaped. Thereafter, the silver epoxy bridge 44 is completed by adding the conductive material to the via on the inside of the cylinder with no additional profile to the finished device.

In order to obtain good performance of the elements and to facilitate re-shaping the flex circuit 2 into a cylinder after the integrated circuit chips 6 and transducer elements 8 have been attached, the transducer elements 8 are physically separated during step 108. Dicing is accomplished by means of a well known high precision, high speed disc sawing apparatus, such as those used for sawing silicon wafers. It is desirable to make the saw kerfs (i.e., the spaces between the adjacent transducer elements) on the order of 15-25 μm when the flex circuit is re-shaped into a cylindrical shape. Such separation dimensions are achieved by known high precision saw blades having a thickness of 10-15 μm.

After the two part epoxy 50 is fully cured, the flex circuit 2 is fixtured in order to facilitate dicing of the transducer material into sixty-four (64) discrete elements. The flex circuit 2 is fixtured by placing the flex circuit 2 onto a vacuum chuck (of well known design for precision dicing of very small objects such as semiconductor wafers) which is raised by 50-200 μm in the region of the transducer elements 8 in order to enable a saw blade to penetrate the flex circuit 2 in the region of the transducer elements 8 without affecting the integrated circuit region. The saw height is carefully controlled so that the cut extends completely through the PZT or PZT composite 40 and partially into the KAPTON substrate 33 of the flex circuit 2 by a few microns. In order to further reduce the conduction of ultrasound to adjacent transducer elements, the cut between adjacent transducer elements may extend further into the flex circuit 2. The resulting transducer element pitch (width) is on the order of 50 μm. In alternative embodiments this cut may extend all the way through the flex circuit 2 in order to provide full physical separation of the transducer elements.

Alternatively the separation of transducer elements may possibly be done with a laser. However, a drawback of using a laser to dice the transducer material is that the laser energy may depolarize the PZT or PZT composite 40. It is difficult to polarize the separated PZT transducer elements, and therefore the sawing method is presently preferred.

After the PZT or PZT composite 40 has been sawed into discrete transducer elements and cleaned of dust arising from the sawing of the PZT or PZT composite 40, at step 110 the integrated circuit chips 6 are flip-chip bonded in a known manner to the flex circuit 2 using pressure and heat to melt the solder bumps such as solder bump 36. The integrated circuit chips 6 are aligned by means of either infrared or visible light alignment techniques so that the Indium solder bumps on the integrated circuits 6 align with the pads on the flex circuit 2. These alignment methods are well known to those skilled in the art. The partially assembled ultrasound transducer assembly is now ready to be formed into a substantially cylindrical shape as shown in FIGS. 2, 3 and 4.

Before re-shaping the flat flex circuit 2 (as shown in FIG. 1) into a cylindrical shape around the lumen tube 18, at step 112 backing material 30 is formed into a cylindrical shape around the lumen tube 18 using a mold. Pre-forming the backing material 30 onto the lumen tube 18, rather than forming the flex circuit 2 and backfilling the cylinder with backing material, helps to ensure concentricity of the transducer portion 12 of the assembled ultrasound transducer device around the lumen tube 18 and facilitates precise forming of the backing material portion of the ultrasound transducer apparatus embodying the present invention.

At step 114, the lumen tube 18, backing material 30, and the partially assembled flex circuit 2 are carefully drawn into a preformed TEFLON mold having very precise dimensions. The TEFLON mold is formed by heat shrinking TEFLON tubing over a precision machined mandrel (as shown in FIG. 8 and described below). The heat shrinkable TEFLON tubing is cut away and discarded after fabrication of the ultrasound transducer assembly is complete. As a result, distortion of a mold through multiple uses of the same mold to complete fabrication of several ultrasound transducer assemblies is not a problem, and there is no clean up of the mold required.

The TEFLON molds incorporate a gentle lead-in taper enabling the sides of the flex circuit 2 to be carefully aligned, and the gap between the first and last elements to be adjusted, as the flex circuit 2 is pulled into the mold. In the region of the transducer, the mold is held to a diametric precision of 2-3 μm. Since the flex circuit 2 dimensions are formed with precision optical techniques, the dimensions are repeatable to less than 1 μm, the gap between the first and last elements (on the outer edges of the flat flex circuit 2) can be repeatable and similar to the kerf width between adjacent elements.

While the flex circuit 2 is drawn into the TEFLON mold during step 114, the KAPTON tube 20 is inserted into the TEFLON mold between the integrated circuits 6 (resting against the outer surface of the KAPTON tube 20) and the lumen tube 18 (on the inside). The KAPTON tube 20 causes the flex circuit 2 to take on a pentagonal cross-section in the electronics portion 14 of the ultrasound transducer assembly by applying an outward radial force upon the integrated circuits 6. The outward radial force exerted by the KAPTON tube 20 upon the integrated circuits 6 causes the flex circuit 2 to press against the TEFLON mold at five places within the cylindrical shape of the TEFLON mold.

A TEFLON bead is placed within the lumen tube 18 in order to prevent filling of the lumen 16 during the steps described below for completing fabrication of the ultrasound transducer assembly. While in the mold, the partially assembled ultrasound transducer assembly is accessed from both open ends of the mold in order to complete the fabrication of the ultrasound transducer assembly.

Next, at step 116 the silver epoxy bridges (e.g., bridge 44) connecting the ground layer of each of the discrete transducers (e.g., ground layer 42) to the ground layer 28 are completed. The connection is completed by injecting silver epoxy into the vias such as via 45 in the KAPTON substrate 33. The bridges are completed by filling the vias after the flex circuit 2 has been re-shaped into a cylinder. However, in alternative fabrication methods, the vias are filled while the flex circuit 2 is still in its flat state as shown in FIG. 1.

The lumen tube 18 is also connected to the ground layer 28 at the distal end of the ultrasound transducer assembly. Alternatively, the lumen tube 18 and ground layer 28 are connected to electrical ground wire of the cable 35 at the proximal end of the ultrasound transducer assembly.

After the ground layer 42 of the transducers is connected to the ground plane 28 and the silver epoxy bridge 44 is cured, at step 118 additional backing material 30 is injected into the distal end of the ultrasound transducer assembly in order to fill the kerfs between transducer elements and any gaps between the preformed portion of the backing material 30 and the transducer elements 8. This ensures that there are no air gaps in the region of the backing material 30 since air gaps degrade the performance of the ultrasound transducer assembly and degrade the mechanical integrity of the device.

At step 120, after the part of the backing material 30 added during step 118 cures, the encapsulating epoxy 22 is injected into the electronics portion 14 of the ultrasound transducer assembly at the end housing the integrated circuit chips 6.

At step 122, after the encapsulating epoxy 22 and backing material 30 are cured, the ultrasound transducer assembly is removed from the mold by either pushing the device out of the mold or carefully cutting the TEFLON mold and peeling it from the ultrasound transducer assembly. The TEFLON bead is removed from the lumen tube 18. Stray encapsulating epoxy or backing material is removed from the device.

Next, at step 124 the device is covered with the PARYLENE coating 32. The thickness of the PARYLENE coating 32 is typically 5-20 μm. The PARYLENE coating 32 protects the electronic circuitry and transducers of the ultrasound transducer assembly and provides a secondary matching layer for the transducer elements 8. The individual conductors of the cable 35 are bonded to the cable pads 10.

Having described one method for fabricating an ultrasound transducer assembly incorporating the flex circuit 2, it is noted that the order of the steps is not necessarily important. For example, while it is preferred to attach the integrated circuits 6 to the flex circuit 2 after the transducers 6 have been bonded to the flex circuit 2, such an order for assembling the ultrasound transducer assembly is not essential. Similarly, it will be appreciated by those skilled in the art that the order of other steps in the described method for fabricating an ultrasound transducer assembly can be re-arranged without departing from the spirit of the present invention.

Turning briefly to FIG. 8, a longitudinal cross-section view is provided of the mandrel previously mentioned in connection with the description of step 114 above. The mandrel enables a TEFLON tube to be re-formed into a mold (shown generally by a ghost outline) having very precise inside dimensions by heat shrinking the TEFLON tube onto the mandrel. The TEFLON mold is thereafter used to re-shape the partially assembled ultrasound transducer assembly during step 114. While precise dimensions and tolerances are provided on the drawing, they are not intended to be limiting since they are associated with a particular size and shape for an ultrasound transducer assembly embodying the present invention.

The mandrel and resulting inside surface of the TEFLON mold generally display certain characteristics. First, the mandrel incorporates a taper from a maximum diameter at the end where the flex circuit enters the mold to a minimum diameter at the portion of the mold corresponding to the transducer portion of the ultrasound transducer assembly. This first characteristic facilitates drawing the flex circuit into the mold.

Second, the mold has a region of constant diameter at the region where the integrated circuit portion will be formed during step 114. This diameter is slightly greater than the diameter of the transducer region of the mold where the diameter of the inside surface is precisely formed into a cylinder to ensure proper mating of the two sides of the flex circuit when the flat, partially assembled transducer assembly is re-shaped into a cylindrical transducer assembly. The greater diameter in the integrated circuit region accommodates the points of the pentagon cross-section created by the integrated circuit chips 6 when the flat flex circuit is re-shaped into a cylinder.

Finally, a second taper region is provided between the integrated circuit and transducer portions of the mold in order to provide a smooth transition from the differing diameters of the two portions.

The above description of the invention has focused primarily upon the structure, materials and steps for constructing an ultrasound transducer assembly embodying the present invention. Turning now to FIGS. 9 and 10, an illustrative example of the typical environment and application of an ultrasound device embodying the present invention is provided. Referring to FIGS. 9 and 10, a buildup of fatty material or plaque 70 in a coronary artery 72 of a heart 74 may be treated in certain situations by inserting a balloon 76, in a deflated state, into the artery via a catheter assembly 78. As illustrated in FIG. 9, the catheter assembly 78 is a three-part assembly, having a guide wire 80, a guide catheter 78*a* for threading through the large arteries such as the aorta 82 and a smaller diameter catheter 78*b* that fits inside the guide catheter 78*a*. After a surgeon directs the guide catheter 78*a* and the guide wire 80 through a large artery leading via the aorta 82 to the coronary arteries, the smaller catheter 78*b* is inserted. At the beginning of the coronary artery 72 that is partially blocked by the plaque 70, the guide wire 80 is first extended into the artery, followed by catheter 78*b*, which includes the balloon 76 at its tip.

Once the balloon 76 has entered the coronary artery 72, as in FIG. 10, an ultrasonic imaging device including a probe assembly 84 housed within the proximal sleeve 86 of the balloon 76 provides a surgeon with a cross-sectional view of the artery on a video display 88. In the illustrated embodiment of the invention, the transducers emit 20 MHz ultrasound excitation waveforms. However, other suitable excitation waveform frequencies would be known to those skilled in the art. The transducers of the probe assembly 84 receive the reflected ultrasonic waveforms and convert the ultrasound echoes into echo waveforms. The amplified echo waveforms from the probe assembly 84, indicative of reflected ultrasonic waves, are transferred along a microcable 90 to a signal processor 92 located outside the patient. The catheter 78*b* ends in a three-part junction 94 of conventional construction that couples the catheter to an inflation source 96, a guide wire lumen and the signal processor 92. The inflation and guide wire ports 94*a* and 94*b*, respectively, are of conventional PTCA catheter construction. The third port 94*c* provides a path for the cable 90 to connect with the signal processor 92 and video display 88 via an electronic connector 98.

It should be noted that the present invention can be incorporated into a wide variety of ultrasound imaging catheter assemblies. For example, the present invention may be incorporated in a probe assembly mounted upon a diagnostic catheter that does not include a balloon. In addition, the probe assembly may also be mounted in the manner taught in Proudian et al. U.S. Pat. No. 4,917,097 and Eberle et al. U.S. Pat. No. 5,167,233, the teachings of which are explicitly incorporated, in all respects, herein by reference. These are only examples of various mounting configurations. Other configurations would be known to those skilled in the area of catheter design.

Furthermore, the preferred ultrasound transducer assembly embodying the present invention is on the order of a fraction of a millimeter to several millimeters in order to fit within the relatively small cross-section of blood vessels. However, the structure and method for manufacturing an ultrasound transducer assembly in accordance with present invention may be incorporated within larger ultrasound devices such as those used for lower gastrointestinal examinations.

Illustrative embodiments of the present invention have been provided. However, the scope of the present invention is intended to include, without limitation, any other modifications to the described ultrasound transducer device and methods of producing the device falling within the fullest legal scope of the present invention in view of the description of the invention and/or various preferred and alternative embodiments described herein. The intent is to cover all alternatives, modifications and equivalents included within the spirit and scope of the invention as defined by the appended claims.

What is claimed is:

1. An ultrasound transducer assembly for facilitating providing images from within a cavity, the ultrasound transducer assembly comprising:

an ultrasound transducer array comprising a set of ultrasound transducer elements, wherein the ultrasound transducer array is substantially cylindrical in shape;

integrated circuitry; and a flexible circuit to which the ultrasound transducer array and integrated circuitry arc attached during fabrication of the ultrasound transducer assembly, the flexible circuit comprising:

a flexible substrate to which the integrated circuitry and transducer elements are attached; and electrically conductive lines deposited upon the flexible substrate for transporting electrical signals between the integrated circuitry and the transducer elements;

wherein the ultrasound transducer array, the integrated circuitry, the flexible circuit, and the flexible substrate are dimensioned for insertion within a blood vessel.

2. The ultrasound transducer assembly of claim 1, having suitable dimensions for providing images of a blood vessel from within a vasculature, and wherein the diameter of the substantially cylindrical ultrasound transducer array is on the order of 0.3 to 5.0 millimeters.

3. The ultrasound transducer assembly of claim 1 wherein the flexible circuit is substantially cylindrical in shape and occupies a relatively outer position than the integrated circuitry with respect to a central axis of the cylindrical ultrasound transducer array.

4. The ultrasound transducer assembly of claim 1 wherein the electrically conductive lines deposited upon the flex circuit occupy a relatively outer position in relation to the transducer elements, with respect to a central axis of the ultrasound transducer assembly in a transducer portion of the ultrasound transducer assembly.

5. The ultrasound transducer assembly of claim 1 wherein the electrically conductive lines deposited upon the flex circuit occupy a relatively outer position in relation to the integrated circuitry, with respect to a central axis of the ultrasound transducer assembly in an electronics portion of the ultrasound transducer assembly.

6. The transducer assembly of claim 1 wherein the substrate comprises a polyimide.

7. The transducer assembly of claim 1 wherein the substrate thickness is substantially within the range of 5 microns to 100 microns.

8. The transducer assembly of claim 1 wherein the layer thickness of the electrically conductive lines is substantially in the range of 2-5 microns.

9. The ultrasound transducer assembly of claim 1 wherein the ultrasound transducer elements comprise PZT material.

10. The ultrasound transducer assembly of claim 9 wherein the PZT material is a PZT composite.

11. The ultrasound transducer assembly of claim 9 wherein the PZT material is directly bonded to conductive material comprising the electrode coupled to a communication channel in the integrated circuitry.

12. The ultrasound transducer assembly of claim 1 wherein the ultrasound transducer elements comprise at least 32 transducer elements.

13. The ultrasound transducer assembly of claim 1 wherein the ultrasound transducer elements comprise at least 48 transducer elements.

14. The ultrasound transducer assembly of claim 1 wherein the ultrasound transducer elements comprise at least 64 transducer elements.

15. A method for fabricating an ultrasound transducer assembly comprising a flexible circuit, integrated circuitry, and a set of transducer elements for facilitating providing images of a blood vessel from within a vasculature, the method comprising the steps:

fabricating the flexible circuit comprising a flexible substrate and a set of electrically conductive lines formed upon the flexible substrate;

constructing the set of transducer elements upon the flexible circuit and attaching the integrated circuitry to the flexible circuit while the flexible circuit is in a substantially flat shape; and re-shaping the flexible circuit into a substantially non-flat shape after the step of constructing a set of transducer elements and attaching the integrated circuitry such that the set of transducer elements are arranged in a circular configuration.

16. The method of claim 15 wherein the set of transducer elements comprise PZT material.

17. The method of claim 16 wherein the step of constructing a set of transducer elements upon the flexible circuit comprises bonding conductive material directly to the PZT material.

18. The method of claim 17 wherein the conductive material bonded directly to the PZT material forms a set of excitation electrodes coupled to the integrated circuitry via the set of electrically conductive lines.

19. An ultrasound transducer assembly for use in intravascular ultrasound applications, the ultrasound transducer assembly comprising:

a flex circuit including a flexible substrate and electrically conductive lines, the flex circuit defining an outer surface and an inner surface;

a plurality of integrated circuits attached to the inner surface of the flex circuit and in communication with the electrically conductive lines; and a plurality of ultrasound transducer elements mounted to the inner surface of the flex circuit in a circular arrangement about a central axis of the ultrasound transducer assembly, the plurality of ultrasound transducers in communication with the electrically conductive lines to facilitate communication of electrical signals between the plurality of ultrasound transducers and the plurality of integrated circuits;

wherein the flex circuit, the plurality of integrated circuits, and the plurality of ultrasound transducer elements are dimensioned for insertion within a blood vessel.

20. The ultrasound transducer assembly of claim 19, wherein the outer surface of the flex circuit has a polygonal profile adjacent to the plurality of integrated circuits and a substantially cylindrical profile adjacent to the plurality of ultrasound transducers.

* * * * *